United States Patent [19]

Asano et al.

[11] Patent Number: 5,686,494
[45] Date of Patent: Nov. 11, 1997

[54] PHARMACEUTICAL PREPARATIONS FOR AMELIORATING EPIGASTRIC FUNCTIONAL DISORDERS

[75] Inventors: Masahide Asano; Kazuhiko Nakajima; Kazuhisa Furuhama; Satoshi Hatanaka; Keiko Kawarabayashi, all of Tokyo, Japan

[73] Assignee: Daiichi Pharmaceutical Co., Ltd., Tokyo, Japan

[21] Appl. No.: 537,910

[22] PCT Filed: Apr. 28, 1994

[86] PCT No.: PCT/JP94/00721

§ 371 Date: Oct. 25, 1995

§ 102(e) Date: Oct. 25, 1995

[87] PCT Pub. No.: WO95/28432

PCT Pub. Date: Oct. 26, 1995

[30] Foreign Application Priority Data

Apr. 28, 1993 [JP] Japan ................. 5-102210

[51] Int. Cl.⁶ .................................................... A61K 31/16
[52] U.S. Cl. .................................................... 514/616
[58] Field of Search .................................................... 514/616

[56] References Cited

U.S. PATENT DOCUMENTS 4,985,595  1/1991  Miki et al. ................. 514/616

*Primary Examiner*—Raymond Henley, III
*Attorney, Agent, or Firm*—Sughrue,Mion,Zinn,Macpeak & Seas, PLLC

[57] ABSTRACT

A pharmaceutical preparation for ameliorating nonulcer dyspepsia (NUD) or epigastric dysfunction complaints is provided. The present invention uses an aminobenzamide compound represented by the following formula (1) or a salt thereof:

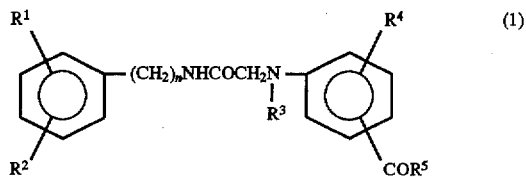

wherein each of $R^1$ and $R^2$ is independently a lower alkoxyl group; $R^3$ is a hydrogen atom, a lower acyl group, a lower alkyl group, a lower alkoxycarbonyl group or a group represented by a formula $—X—SO_3M$ where X is a lower alkylene group and M is an alkali metal or an alkaline earth metal; $R^4$ is a hydrogen atom, a halogen atom or a lower alkoxyl group; $R^5$ is an amino group, a morpholino group or a lower alkylamino group, where the alkyl moiety of the lower alkylamino group may have a hydroxyl group; and n is an integer of 1 to 6.

15 Claims, No Drawings

PHARMACEUTICAL PREPARATIONS FOR AMELIORATING EPIGASTRIC FUNCTIONAL DISORDERS

This application is a 371 of PCT/JP94/00721 filed Apr. 28, 1994.

This invention relates to pharmaceutical preparations for the amelioration of nonulcer dyspepsia (NUD) (or epigastric dysfunction)-related complaints.

BACKGROUND OF THE INVENTION

Among ailments conventionally diagnosed as chronic gastritis, chronic symptoms may occur in the epigastric area despite the absence of morphological changes in the digestive system has recently been given a concept of "non-ulcer dyspepsia (NUD)" which occurs due to an abnormal motility of the digestive tract.

Epigastric dysfunction related complaints with the absence of morphological changes in the digestive tracts, such as gastric heaviness, nausea, vomiting, anorexia, abdominal distension, heartburn, epigastric pain, and eructation, are called "digestive system or NUD-related complaints". Though therapeutic drugs for gastritis have been generally used for the treatment in patients with such symptoms, their actions are not satisfactory. In recent years, digestive tract motility regulating agents such as cisapride (a digestive tract motility activation regulating agent) and, trimebutine maleate (a digestive tract motility adjusting agent) became commonly used in the field of the treatment of such complaints, but their efficacy are not sufficient.

With the aim of providing a digestive tract motility regulating agent which is superior to the aforementioned known agents, the inventors of the present invention have conducted extensive studies and found that an aminobenzamide compound or a salt thereof which is known to be useful as an anti-peptic ulcer agent having an excellent antiulcer effect (JP-A-55-31027, JP-A-56-18947, JP-A-61-267542, EP-A-9608, EP-A-185368, and U.S. Pat. Nos. 4,297,357 and 4,985,595; the term "JP-A" as used herein means an "unexamined published Japanese patent application") also has a digestive tract motility regulating action and is useful as an agent for ameliorating NUD (or epigastric dysfunction complaints) and as a digestive tract motility regulating agent. The present invention has been accomplished on the basis of this finding.

DISCLOSURE OF THE INVENTION

The present invention relates to a pharmaceutical preparation for the amelioration of NUD (or epigastric dysfunction)-related complaints, which contains as an active ingredient an aminobenzamide compound represented by the following formula (1) or a salt thereof:

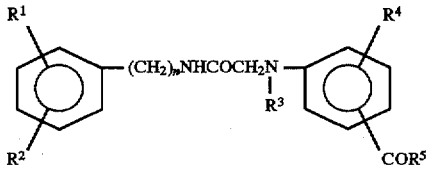

wherein each of $R^1$ and $R^2$ is independently a lower alkoxyl group; $R^3$ is a hydrogen atom, a lower acyl group, a lower alkyl group, a lower alkoxycarbonyl group or a group represented by the formula $-X-SO_3M$ where X is a lower alkylene group and M is an alkali metal or an alkaline earth metal; $R^4$ is a hydrogen atom, a halogen atom or a lower alkoxyl group; $R^5$ is an amino group, a morpholino group or a lower alkylamino group, where the alkyl moiety of the lower alkylamino group may have a hydroxyl group; and n is an integer of 1 to 6.

The present invention further relates to a pharmaceutical preparation for the amelioration of NUD (or epigastric dysfunction complaints) of chronic gastritis, which contains as an active ingredient an aminobenzamide compound represented by formula (1) or a salt thereof;

a pharmaceutical preparation for the amelioration of NUD (or epigastric dysfunction complaints) chronic gastritis, which contains as an active ingredient an aminobenzamide compound represented by formula (1) or a salt thereof;

a pharmaceutical preparation for the treatment of digestive system indefinite complaints, which contains as an active ingredient an aminobenzamide compound represented by formula (1) or a salt thereof; and a pharmaceutical preparation for the treatment of non-ulcer dyspepsia, which contains as an active ingredient an aminobenzamide compound represented by formula (1) or a salt thereof.

The present invention further relates to a pharmaceutical preparation for the regulation of digestive tract motility, which contains as an active ingredient an aminobenzamide compound represented by formula (1) or a salt thereof;

a pharmaceutical preparation for the regulation of gastric motility, which contains as an active ingredient an aminobenzamide compound represented by formula (1) or a salt thereof;

a pharmaceutical preparation for the acceleration of gastric motility, which contains as an active ingredient an aminobenzamide compound represented by formula (1) or a salt thereof;

a pharmaceutical preparation for the regulation of gastric emptying, which contains as an active ingredient an aminobenzamide compound represented by formula (1) or a salt thereof; and a pharmaceutical preparation for the acceleration of gastric emptying, which contains as an active ingredient an aminobenzamide compound represented by formula (1) or a salt thereof.

The present invention further relates to pharmaceutical preparations for (1) the amelioration of NUD (or epigastric dysfunction complaints), (2) the amelioration of digestive system-related symptoms of gastritis, (3) the amelioration of NUD (or epigastric dysfunction complaints) of chronic gastritis, (4) the treatment of digestive system indefinite complaints and (5) the treatment of non-ulcer dyspepsia, in which the active ingredient is 3-[[[2-(3,4-dimethoxyphenyl)ethyl]carbamoyl]methyl]amino-N-methylbenzamide.

The present invention further relates to pharmaceutical preparations for (1) the regulation of digestive tract motility, (2) the regulation of gastric motility, (3) the acceleration of gastric motility, (4) the regulation of gastric emptying, and (5) the acceleration of gastric emptying, in which the active ingredient is 3-[[[2-(3,4-dimethoxyphenyl)ethyl]carbamoyl]methyl]amino-N-methylbenzamide.

The present invention further relates to a pharmaceutical composition in a unit dosage form, which contains an aminobenzamide compound represented by formula (1) or a salt thereof in an amount per unit dose effective for regulating digestive tract motility of the vertebrate having abnormal digestive tract motility.

For this pharmaceutical composition, the aminobenzamide compound represented by formula (1) or a salt thereof is preferably 3-[[[2-(3,4-dimethoxyphenyl)ethyl]carbamoyl]methyl]amino-N-methylbenzamide or a salt thereof, and the pharmaceutical composition is particularly useful for regulating digestive tract emptying of vertebrate having an abnormal digestive tract motility.

In addition, the present invention relates to a method of regulating digestive tract motility comprising administering an aminobenzamide compound represented by the formula (1) or a salt thereof in an amount effective for regulating digestive tract motility of the vertebrate having abnormal digestive tract motility.

In this method, the aminobenzamide compound represented by formula (1) or a salt thereof is preferably 3-[[[2-(3,4-dimethoxyphenyl)ethyl]carbamoyl]methyl]amino-N-methylbenzamide or a salt thereof. The method is particularly useful when the abnormal digestive tract motility is abnormal gastric motility.

The term "pharmaceutical preparation for the amelioration of NUD (or epigastric dysfunction complaints)" as used herein means a preparation for the amelioration of human clinical symptoms based on the concept of "digestive system indefinite complaints".

The term "NUD (or epigastric dysfunction) complaints" means symptoms having digestive system-related symptoms found in patients despite the absence of morphological changes in the digestive system, such as gastric oppression, nausea, vomiting, anorexia, abdominal distension, heartburn, epigastric pain, eructation and the like.

The term "pharmaceutical preparation for the amelioration of NUD (or epigastric dysfunction complaints) of gastritis" as used herein means a preparation for the amelioration of the above-described symptoms caused by gastritis, and the term "pharmaceutical preparation for the amelioration of NUD (or epigastric dysfunction complaints) in chronic gastritis" as used herein means a preparation for the amelioration of the above-described symptoms caused by chronic gastritis.

The term "gastritis" as used herein generally means gastric wall inflammatory diseases, mainly non-specific mucosal inflammations, which are divided into acute gastritis and chronic gastritis depending on the circumstances. Chronic gastritis is further divided, generally by the classification of R. Schindler, into superficial gastritis, atrophic gastritis and hypertrophic gastritis.

Next, pharmaceutical preparations of the present invention for the regulation of digestive tract motility, or pharmaceutical compositions containing the same, pharmaceutical preparations for the regulation of gastric motility, for the acceleration of gastric motility, for the regulation of gastric emptying, and for the acceleration of gastric emptying, and the method of regulating digestive tract motility according to the present invention are described.

The term "regulation of digestive tract motility" as used herein means acceleration and control of the motility function of digestive tracts such as the esophagus, the stomach, the small intestine, the large intestine and the like, where the term "motility function" means, in the case of the stomach for example, functions for the emptying, mixing and the like of the gastric content. A drug capable of regulating these functions is herein called "pharmaceutical preparation for the regulation of digestive tract motility". These functions have been confirmed in mice and similar experimental animals by quantitative measurement of Phenol Red administered as an index of the gastric content.

The term "regulation of gastric motility" as used herein means the acceleration and control of the motility function of digestive tracts, particularly the stomach, and a drug capable of regulating these functions is herein called "pharmaceutical preparation for the regulation of gastric motility".

The term "regulation of gastric emptying" as used herein means a function to evacuate contents in the stomach such as food and partial digests thereof from the pylorus, and a drug capable of regulating such function is herein called "pharmaceutical preparation for the regulation of gastric emptying".

The method of regulating digestive tract motility according to the present invention comprises administrating an effective amount of the compound of formula (1) to the vertebrate including human to regulate digestive tract motility and the effective amount is the amount effective to regulate the above-described digestive tract motility.

The aminobenzamide compound, which is the active ingredient of the pharmaceutical preparations for ameliorating NUD (or epigastric dysfunction complaints) according to the present invention, is known to have an antiulcer effect. However, the antiulcer effect is quite different from the function to improve digestive system indefinite complaints disclosed in the present invention.

The function of the aminobenzamide compound, which is an active ingredient of the pharmaceutical preparation for ameliorating NUD (or epigastric dysfunction complaints) according to the present invention, i.e., amelioration of digestive system indefinite complaints, is effected by ameliorating gastric emptying hypofunction, which is the cause of digestive system indefinite complaints. On the other hand, the antiulcer effect of the aminobenzamide compound, which is an active ingredient of the pharmaceutical preparation for ameliorating NUD (or epigastric dysfunction complaints) according to the present invention, is based on the increase in gastric mucosal blood flow (cf. Arzneim.-Forsch./Drug Res. 40 (I), 3, 276–281 (1990)), and thus has no direct relation with the gastric emptying accelerating action according to the present invention.

With respect to the relationship between gastric emptying and the various digestive system diseases including ulcers and epigastric indefinite complaints, it has been reported that only slight gastric emptying hypofunction is observed in gastric ulcers while the gastric emptying hypofunction is remarkable in epigastric indefinite complaints (cf. Pharma Medica Vol. 8, 57–63 (1990)).

Accordingly, it can be considered that abnormal motility of the digestive tract has almost no relationship with ulcer but the digestive tract indefinite complaints are caused by the abnormal motility of the digestive tract.

In addition, it is also a great difference that ulcers are accompanied by morphological changes while digestive tract indefinite complaints are not.

The following describes substituent groups in the aminobenzamide compound represented by the aforementioned formula (1).

Illustrative examples of the lower alkoxyl group in the formula (1) include methoxy, ethoxy, propoxy, butoxy, pentyloxy, hexyloxy and similar groups.

Illustrative examples of the lower acyl group in the formula (1) include acetyl, propionyl, butyryl, isobutyryl, valeryl, isovaleryl, pivaloyl, hexanoyl and similar groups.

Illustrative examples of the lower alkyl group in the formula (1) include methyl, ethyl, propyl, isopropyl, butyl, tert-butyl, pentyl, hexyl and similar groups.

Illustrative examples of the lower alkylene group in the formula (1) include methylene, ethylene, propylene, butylene, amylene, hexylene and similar groups.

The lower alkylamino group in the formula (1) is a lower monoalkylamino group or a lower dialkylamino group, where the lower alkyl moieties of the lower dialkylamino group may be the same or different from each other.

Illustrative examples of the salt of the aminobenzamide compound represented by the formula (1) include acid addition salts with inorganic acids such as hydrochloric acid, sulfuric acid and the like or with organic acids such as picric acid and the like.

The aminobenzamide compound and salts thereof according to the present invention can be produced by the process disclosed in JP-A-55-31027, JP-A-56-18947, JP-A-61-267542, EP-A-9608, EP-A-185368, and U.S. Pat. Nos. 4,297,357 and 4,985,595, herein incorporated by reference.

The following 9 compounds {A} to {I} are illustrative examples of the aminobenzamide compound of the present invention.

{A} 3-[[[2-(3,4-dimethoxyphenyl)ethyl]carbamoyl]methyl]-amino-N/methylbenzamide

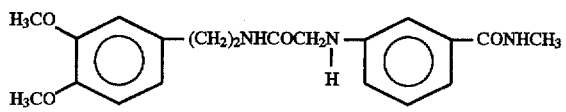

{B} 3-[[[2-(3,4-dimethoxyphenyl)ethyl]carbamoyl]methyl]-amino-N-ethylbenzamide

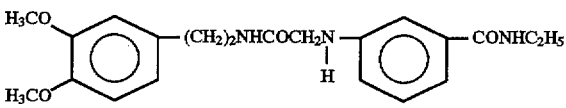

{C} 3-[[[2-(3,4-dimethoxyphenyl)ethyl]carbamoyl]methyl]-amino-N,N-dimethylbenzamide

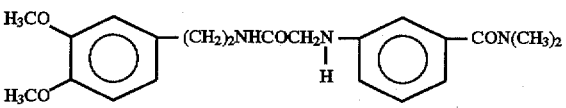

{D} 3-[[[2-(3,4-dimethoxyphenyl)ethyl]carbamoyl]methyl]-amino-N-(2-hydroxyethyl)benzamide

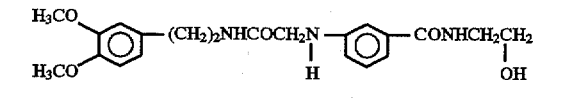

{E} 1-[3-[[[2-(3,4-dimethoxyphenyl)ethyl]carbamoyl]methyl]-amino]benzoylmorpholine

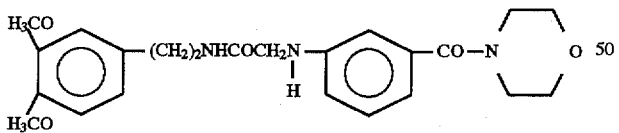

{F} 2-[[[2-(3,4-dimethoxyphenyl)ethyl]carbamoyl]methyl]-amino-4-methoxy-N-methylbenzamide

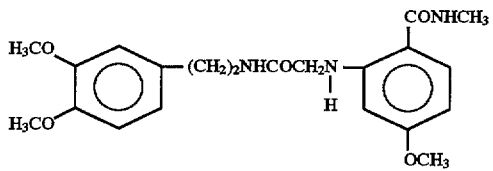

{G} 2-[[[2-(3,4-dimethoxyphenyl)ethyl]carbamoyl]methyl]-amino-5-methoxy-N-methylbenzamide

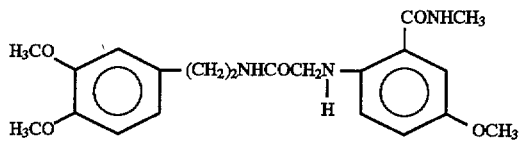

{H} 2-[[[2-(3,4-dimethoxyphenyl)ethyl]carbamoyl]methyl]amino-N-methylbenzamide

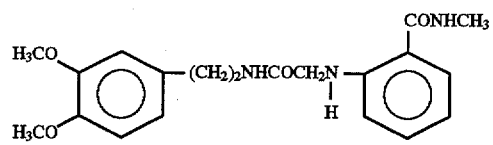

{I} Sodium salt of 3-[N-sulfomethyl-N-[[[2-(3,4-dimethoxyphenyl)ethyl]carbamoyl]methyl]amino]benzamide

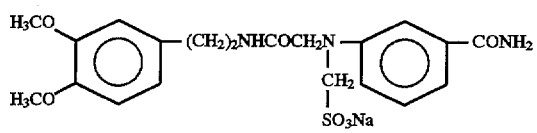

In the present invention, nomenclature of the illustrative aminobenzamide compounds may be different from those used in JP-A-55-31027, JP-A-56-18947, JP-A-61-267542, EP-A-9608, EP-A-185368, and U.S. Pat. Nos. 4,297,357 and 4,985,595, but these illustrative compounds are the same compounds disclosed therein.

Of these illustrative examples, the representative compound is compound {A}, which is generally called "ecabapide".

The pharmaceutical preparation of the present invention for the amelioration of NUD (or epigastric dysfunction complaints) or the regulation of digestive tract motility is used as a drug for the amelioration of NUD (or epigastric dysfunction complaints) in gastritis, especially in chronic gastritis, or as a drug for the regulation of motility in digestive tracts such as the esophagus, the stomach, the small intestine, the large intestine and the like, especially as a gastric motility regulating drug, more particularly as a gastric emptying regulating drug.

The pharmaceutical preparation of the present invention for the amelioration of NUD (or epigastric dysfunction complaints) or the regulation of digestive tract motility can be administered by oral or parenteral administration, but preferably by oral administration.

The pharmaceutical preparation of the present invention for the amelioration of NUD (or epigastric dysfunction complaints) or the regulation of digestive tract motility can be made into various dosage forms by known preparation techniques. Appropriate additives such as vehicles, binders, disintegrators and the like can be added to the preparations.

Examples of the vehicles, binders, disintegrators which can be used as additives are described below.

Examples of useful vehicles include lactose, starch, crystalline cellulose, light silicic acid anhydride and the like.

Examples of useful binders include crystalline cellulose, mannitol, dextrin, hydroxypropylcellulose, polyvinylpyrrolidone and the like.

Examples of useful disintegrators include starch, carboxymethylcellulose, carboxymethylcellulose calcium and the like.

These additive agents should be used in the inventive pharmaceutical preparation in such an amount that they are not toxic within the dosage range of the preparation, and do not spoil the therapeutic effects of the active ingredient contained in the preparation.

The pharmaceutical preparation of the present invention for the amelioration of NUD (or epigastric dysfunction complaints) or the regulation of digestive tract motility may typically be made into an oral dosage form such as capsules, granules, fine granules, pills, powders, tablets and the like, of which fine granules and tablets are particularly preferred.

The pharmaceutical preparation of the present invention for the amelioration of NUD (or epigastric dysfunction complaints) or the regulation of digestive tract motility may be administered in a dose of generally from 30 to 600 mg of the active ingredient per day per adult, preferably from 75 to 600 mg/day/adult, more preferably 300 mg/day/adult.

When the pharmaceutical preparation of the present invention for the amelioration of NUD (or epigastric dysfunction complaints) or the regulation of digestive tract motility is provided in an oral dosage form, it may be administered before, during or after meals, once a day or 2 to 3 times a day by dividing the daily dose accordingly.

The aminobenzamide compound or a salt thereof according to the present invention has an extremely low toxicity, because its $LD_{50}$ value after oral administration evaluated in a mouse acute toxicity test is 2 g/kg or more (JP-A-55-31027, JP-A-56-18947, JP-A-61-267542, EP-A-9608, EP-A-185368, and U.S. Pat. Nos. 4,297,357 and 4,985,595), and therefore is a compound which can be safely administered to humans.

BEST MODE FOR CARRYING OUT THE INVENTION

The following Examples and Test Examples are provided to further illustrate the present invention, but the present invention should not be limited thereto. In the following Examples and Test Examples, the aforementioned compound A, namely 3-[[[2-(3,4-dimethoxyphenyl)ethyl]carbamoyl]methyl]amino-N-methylbenzamide, was used.

EXAMPLE 1

Uncoated tablets of the following formulation were prepared in accordance with the procedure disclosed in "Tablets", General Rules for Preparations, *Japanese Pharmacopeia*.

| Component | Amount |
| --- | --- |
| Compound A | 100 mg |
| Vehicle | 73 mg |
| Disintegrator | 6 mg |
| Binder | 7 mg |
| Lubricant | 4 mg |
| Pigment | trace |
| Total/tablet | 190 mg |

Each of the thus prepared uncoated tablets was coated with 10 mg of a membrane mainly composed of a water soluble film base, and used as a test pharmaceutical preparation.

EXAMPLE 2

Uncoated tablets of the following formulation were prepared in accordance with the procedure disclosed in "Tablets", General Rules for Preparations, *Japanese Pharmacopeia*.

| Component | Amount |
| --- | --- |
| Compound A | 100 mg |
| Vehicle | 38 mg |
| Disintegrator | 5 mg |
| Binder | 5 mg |
| Lubricant | 2 mg |
| Pigment | trace |
| Total/tablet | 150 mg |

Each of the thus prepared uncoated tablets was coated with 8 mg of a membrane mainly composed of a water soluble film base, and used as a test pharmaceutical preparation.

EXAMPLE 3

Uncoated tablets of the following formulation were prepared in accordance with the procedure disclosed in "Tablets", General Rules for Preparations, *Japanese Pharmacopeia*.

| Component | Amount |
| --- | --- |
| Compound A | 100 mg |
| Vehicle | 9 mg |
| Disintegrator | 6 mg |
| Binder | 4 mg |
| Lubricant | 1 mg |
| Pigment | trace |
| Total/tablet | 120 mg |

Each of the thus prepared uncoated tablets was coated with 7 mg of a membrane mainly composed of a water soluble film base, and used as a pharmaceutical test preparation.

[Test Example]

TEST EXAMPLE 1

Effect on gastric emptying in cholecystokinin (CCK)-induced delayed gastric emptying model (Phenol red method)

After overnight fasting, male Slc:ddY mice of 6 to 7 weeks of age (body weight, 20 to 30 g; SLC, Shizuoka, Japan) were divided into six groups: a group in which cholecystokinin was administered with no drug treatment (No. 1 in Table 1), groups in which cholecystokinin was administered after administration of compound A (Nos. 2 to 4), a group in which cholecystokinin was administered after administration of cisapride as a positive control (No. 5) and a group in which cholecystokinin and drug treatments were not made (No. 6). Five to 15 mice were used in each group.

First, 90 minutes before the administration of phenol red, 1 mg/kg, 3 mg/kg or 10 mg/kg of compound A suspended in 0.5% carboxymethylcellulose was orally administered to mice of the compound A administration groups, respectively, (Nos. 2 to 4), 3 mg/kg of cisapride suspended in 0.5% carboxymethylcellulose was orally administered to mice as the positive control drug administration group (No. 5) and 0.5% carboxymethylcellulose was orally administered to mice of the compound A administration group with no drug treatment (No. 1) and the no drug and no cholecystokinin treatment group (No. 6). Next, 5 minutes before the phenol red administration, 5 μg/kg of cholecystokinin (CCK8s, manufactured by Sigma) which had been dissolved in distilled water and then diluted with physiological saline was intraperitoneally administered to mice of each group. Thereafter, phenol red dissolved in 1% methylcellulose was orally administered with a dose of 0.2 mg/0.3 ml/mouse. After 30 minutes of the phenol red administration, each mouse was sacrificed by cervical dislocation to excise the stomach, and the amount of phenol red remaining in the excised stomach was measured to calculate the gastric emptying rate (%) by the following formula.

Gastric emptying rate (%)=[1-(phenol red recovered from drug-applied mouse/X)]×100

(X is the average value of the recovered phenol red remaining in the stomach excised from each mouse sacrificed just after the phenol red administration)

TABLE 1

| Group No. | Drug (90 min before PR administration) | CCK administration (5 min before PR administration) | Gastric emptying rate (%) |
|---|---|---|---|
| 1 | — | + | 21.3 ± 3.2 |
|   | Compound A |   |   |
| 2 | 1 mg/kg | + | 24.8 ± 2.1 |
| 3 | 3 mg/kg | + | 27.6 ± 4.2 |
| 4 | 10 mg/kg | + | 40.5 ± 6.9 |
|   | Cisapride |   |   |
| 5 | 3 mg/kg | + | 36.7 ± 6.8 |
| 6 | — | − | 78.5 ± 5.9 |

(Note) In mice of all groups (Nos. 1 to 6), each drug was administered 90 minutes before the administration of PR (phenol red), and CCK (cholecystokinin) was administered 5 minutes before the PR administration. Gastric emptying a rate was measured 30 minutes after the PR administration.

As clearly illustrated by Table 1, the gastric emptying rate in mice was reduced to ⅓ or lower by intraperitoneal administration of 5 μg/kg cholecystokinin. In comparison with these mice with a reduced gastric emptying rate, the gastric emptying rate in mice was improved in a dose dependent fashion when the compound A was administered in a dosage of 1 mg/kg, 3 mg/kg or 10 mg/kg.

TEST EXAMPLE 2

Effect on gastric emptying in dopamine-induced delayed gastric emptying model (phenol red method)

After overnight fasting, male Slc:ddY mice of 6 to 7 weeks of age (body weight, 28 to 32 g; SLC, Shizuoka, Japan) were divided into 7 groups, namely a group in which dopamine was administered with no drug treatment (No. 1 in Table 2), groups in which dopamine was administered after administration of the compound A (Nos. 2 to 5), a group in which dopamine was administered after administration of cisapride as a positive control (No. 6) and a group in which dopamine and drug treatments were not made (No. 7). Seven mice were used in each group.

First, 90 minutes before the administration of phenol red, 0.01 mg/kg, 0.03 mg/kg, 0.1 mg/kg or 0.3 mg/kg of the compound A suspended in 0.5% carboxymethylcellulose was orally administered to mice of the compound A administration groups (Nos. 2 to 5), 3 mg/kg of cisapride suspended in 0.5% carboxymethylcellulose was orally administered to mice as the positive control drug administration group (No. 6) and 0.5% carboxymethylcellulose was orally administered to mice as the dopamine administration group with no drug treatment (No. 1) and the no drug and no dopamine treatment group (No. 7). Next, 5 minutes before the phenol red administration, 30 mg/kg of dopamine which has been dissolved in distilled water and then diluted with physiological saline was intraperitoneally administered to mice of each group. Thereafter, phenol red dissolved in 1% methylcellulose was orally administered with a dose of 0.2 mg/0.3 ml/mouse. After 30 minutes of the phenol red administration, each mouse was sacrificed by cervical dislocation to excise the stomach, and the amount of phenol red remained in the excised stomach was measured to calculate gastric emptying rate (%) by the following formula.

Gastric emptying rate (%)=[1-(phenol red recovered from drug-applied mouse/X)]×100

(X is an average value of the recovered phenol red remained in the stomach excised from each mouse sacrificed just after the phenol red administration)

TABLE 2

| Group No. | Drug (90 min before PR administration) | Administration of dopamine (5 min before PR administration) | Gastric emptying rate (%) |
|---|---|---|---|
| 1 | — | + | 2.4 ± 2.4 |
|   | Compound A |   |   |
| 2 | 0.01 mg/kg | + | 6.9 ± 4.7 |
| 3 | 0.03 mg/kg | + | 21.2 ± 6.1 |
| 4 | 0.1 mg/kg | + | 18.1 ± 8.3 |
| 5 | 0.3 mg/kg | + | 36.2 ± 10.2 |
|   | Cisapride |   |   |
| 6 | 3 mg/kg | + | 23.4 ± 6.6 |
| 7 | — | − | 52.2 ± 10.2 |

(Note) In mice of all groups (Nos. 1 to 7), each drug was administered 90 minutes before the administration of PR (phenol red), and dopamine was administered 5 minutes before the PR administration. Gastric emptying a rate was measured 30 minutes after the PR administration.

As clearly illustrated by Table 2, the gastric emptying rate in mice was reduced to 1/20 or lower by intraperitoneal administration of 30 mg/kg dopamine. In comparison with these mice with reduced gastric emptying rate, the gastric emptying rate in mice was improved when compound A was administered in a dosage of 0.01 mg/kg, 0.03 mg/kg, 0.1 mg/kg or 0.3 mg/kg.

TEST EXAMPLE 3

Effects on subjective symptoms and gastric emptying in patients

A total of 8 patients diagnosed as chronic gastritis and the like without morphological changes in the stomach were examined in this test, each patient complaining of medium or more intense chronic epigastric fullness, having other NUD (or epigastric dysfunction complaints) such as gastric oppression, nausea, vomiting, anorexia, heartburn and the like and also showing delayed gastric emptying.

Each patient was allowed to take 2 tablets of the test pharmaceutical preparation of Example 1 three times a day 15 to 30 minutes before morning, noon and evening meals (600 mg of compound A/day), and the administration was continued for 2 weeks. Subjective symptoms (Table 3) were checked before and 2 weeks after the administration and gastric emptying (Table 4) was checked before and 2 weeks after the administration.

Subjective symptoms were examined by checking existence of the symptoms before and 2 weeks after the administration.

Gastric emptying was examined in accordance with the acetaminophen method of Heading et al (cf. *Br. J. Pharmacol.* 47 415–421 (1973)). That is, each patient after overnight fasting with no drug administration was allowed to take a test food (200 ml of a liquid natural food OKUNOS-A, thoroughly mixed with 1.5 g of acetaminophen) at 9 a.m. and then to take a seat without eating and drinking until completion of the examination. Heparinized blood samples were collected before and 45 minutes after the administration. Thereafter, serum was separated from each sample to measure serum acetaminophen concentration by a high performance liquid chromatography (HPLC). The results are shown in Tables 3 and 4.

TABLE 3

| Symptoms | Cases[a] tested | Symptom-disappeared cases[b] /tested cases[a] |
|---|---|---|
| Epigastralgia | 4 | 4/4 |
| Gastric disphoria | 4 | 4/4 |
| Abdominal distension | 7 | 7/7 |
| Anorexia | 3 | 3/3 |
| Heartburn | 2 | 2/2 |
| Nausea | 4 | 4/4 |
| Vomiting | 3 | 3/3 |

(Note) When the same patient complained of a plurality of symptoms, they were added to respective cases.
[a]:number of cases before administration
[b]:symptom-disappeared cases 2 weeks after administration

TABLE 4

| | Serum acetaminophen concentration (μg/ml) | |
|---|---|---|
| No. | Before administration | After administration |
| 1 | 7.6 | 7.6 |
| 2 | 8.4 | 10.1 |
| 3 | 8.0 | 12.8 |
| 4 | 6.1 | 7.8 |
| 5 | 6.9 | 7.3 |
| 6 | 6.6 | 8.1 |
| 7 | 5.2 | 8.5 |
| 8 | 4.6 | 7.1 |

As shown in Tables 3 and 4, administration of the compound A to patients of No. 1 to No. 8 resulted in the complete disappearance of subjective symptoms after 2 weeks of the administration and the amelioration of gastric emptying in 7 of the 8 cases.

INDUSTRIAL APPLICABILITY

Since the inventive aminobenzamide compound or a salt thereof shows excellent effectiveness in ameliorating NUD (or epigastric dysfunction) symptoms or regulating digestive tract motility, it is markedly useful as a pharmaceutical preparation for the amelioration of NUD (or epigastric dysfunction) or the regulation of digestive tract motility.

We claim:

1. A method for ameliorating nonulcer dyspepsia (NUD) comprising administering to a vertebrate afflicted with NUD an effective amount of an aminobenzamide compound represented by the following formula (1) or a salt thereof:

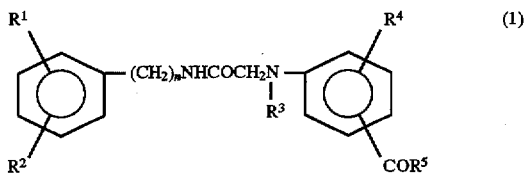

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—SO$_3$M, where X is a lower alkylene group and M is an alkalimetal or an alkarine earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

2. The method according to claim 1, wherein the compound represented by formula (1) is 3-[[[2-(3,4-dimethoxyphenyl)ethyl]carbamoyl]methyl]amino-N-methylbenzamide.

3. A method for treating epigastric dysfunction complaints comprising administering to a vertebrate afflicted with said complaints an effective amount of an aminobenzamide compound represented by the following formula (1) or a salt thereof:

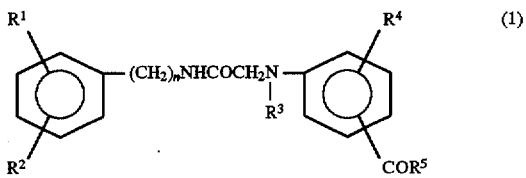

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—SO$_3$M, where X is a lower alkylene group and M is an alkalimetal or an alkaline earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

4. The method according to claim 3, wherein the compound represented by formula (1) is 3-[[[2-(3,4-dimethoxyphenyl)ethyl]carbamoyl]methyl]amino-N-methylbenzamide.

5. The method according to claim 3, wherein the epigastric dysfunction complaints arise from chronic gastritis.

6. A method for regulating digestive tract motility comprising administering to a vertebrate having abnormal digestive tract motility an effective amount of an aminobenzamide compound represented by the following formula (1) or a salt thereof:

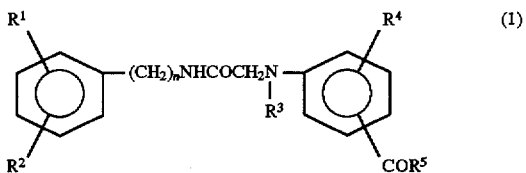

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—SO$_3$M, where X is a lower alkylene group and M is an alkalimetal or an alkaline earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

7. The method according to claim 6, wherein the compound represented by formula (1) is 3-[[[2-(3,4-dimethoxyphenyl)ethyl]carbamoyl]methyl]amino-N-methylbenzamide.

8. A method for regulating gastric motility comprising administering to a vertebrate having abnormal gastric motility an effective amount of an aminobenzamide compound represented by the following formula (1) or a salt thereof:

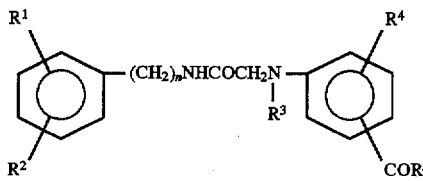

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—$SO_3$M, where X is a lower alkylene group and M is an alkalimetal or an alkaline earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

9. The method according to claim 8, wherein the compound represented by formula (1) is 3-[[[2-(3,4-dimethoxyphenyl)ethyl]carbamoyl]methyl]amino-N-methylbenzamide.

10. A method for accelerating gastric motility comprising administering to a vertebrate in need of accelerated gastric motility an effective amount of an aminobenzamide compound represented by the following formula (1) or a salt thereof:

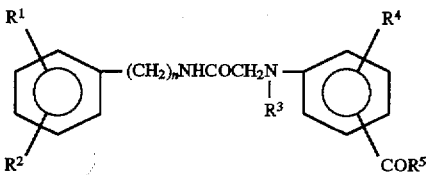

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—$SO_3$M, where X is a lower alkylene group and M is an alkalimetal or an alkaline earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

11. The method according to claim 10, wherein the compound represented by formula (1) is 3-[[[2-(3,4-dimethoxyphenyl)ethyl]carbamoyl]methyl]amino-N-methylbenzamide.

12. A method for regulating gastric emptying comprising administering to a vertebrate having abnormal gastric emptying an effective amount of an aminobenzamide compound represented by the following formula (1) or a salt thereof:

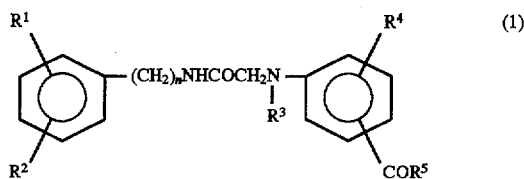

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—$SO_3$M, where X is a lower alkylene group and M is an alkalimetal or an alkaline earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

13. The method according to claim 12, wherein the compound represented by formula (1) is 3-[[[2-(3,4-dimethoxyphenyl)ethyl]carbamoyl]methyl]amino-N-methylbenzamide.

14. A method for accelerating gastric emptying comprising administering to a vertebrate in need of accelerated gastric emptying an effective amount of an aminobenzamide compound represented by the following formula (1) or a salt thereof:

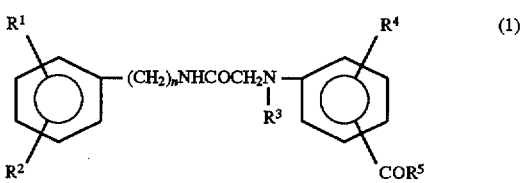

wherein each of $R^1$ and $R^2$ is independently a lower alkoxyl group; $R^3$ is a hydrogen atom, a lower acyl group, a lower alkyl group, a lower alkoxycarbonyl group or a group represented by a formula —X—$SO_3$M, where X is a lower alkylene group and M is an alkalimetal or an alkaline earth metal; $R^4$ is a hydrogen atom, a halogen atom or a lower alkoxy group; $R^5$ is an amino group, a morpholino group or a lower alkylamino group, where the alkyl moiety of said lower alkylamino group may have a hydroxyl group; and n is an integer of 1 to 6.

15. The method according to claim 14, wherein the compound represented by formula (1) is 3-[[[2-(3,4-dimethoxyphenyl)ethyl]carbamoyl]methyl]amino-N-methylbenzamide.

\* \* \* \* \*